United States Patent [19]

Whyte

[11] 4,209,417

[45] Jun. 24, 1980

[54] PERFUMED PARTICLES AND DETERGENT COMPOSITION CONTAINING SAME

[75] Inventor: David D. Whyte, Cincinnati, Ohio

[73] Assignee: The Procter & Gamble Company, Cincinnati, Ohio

[21] Appl. No.: 714,061

[22] Filed: Aug. 13, 1976

[51] Int. Cl.[2] .......................... C11B 9/00; A61K 7/46

[52] U.S. Cl. .......................... 252/174.11; 252/522 A; 252/DIG. 1; 424/76

[58] Field of Search ............... 252/522, 89 R, DIG. 1; 424/76

[56] References Cited

U.S. PATENT DOCUMENTS

| | | | |
|---|---|---|---|
| 3,567,119 | 3/1971 | Wilbert | 424/76 X |
| 3,772,215 | 11/1973 | Gould et al. | 252/522 |

FOREIGN PATENT DOCUMENTS

| | | |
|---|---|---|
| 825293 | 12/1951 | Fed. Rep. of Germany . |
| 115693 | 10/1975 | German Democratic Rep. |

OTHER PUBLICATIONS

English Translation of German Pat. No. 825,293, Dec. 17, 1951, 4 pp.

English Translation of E. German Pat. 115,693, Oct. 12, 1975, 5 pp.

*Primary Examiner*—Thomas J. Herbert, Jr.
*Attorney, Agent, or Firm*—Jerry J. Yetter; Julius P. Filcik; Richard C. Witte

[57] ABSTRACT

Heavily perfumed particles having both immediate and long lasting perfume emitting properties consist essentially of from 30% to 70% water-insoluble perfume, from 25% to 65% of a water-soluble polymer, and emulsifier. The particles are comprised of a continuous polymeric matrix having dispersed substantially uniformly therethrough perfume/emulsifier droplets. The perfumed particles are especially useful in detergent compositions.

19 Claims, No Drawings

PERFUMED PARTICLES AND DETERGENT COMPOSITION CONTAINING SAME

BACKGROUND OF THE INVENTION

This invention relates to heavily perfumed particles and their use in detergent compositions. More particularly it relates to perfume particles having both immediate and long lasting perfume emitting properties.

The use of perfume in various consumer products for aesthetic reasons is well known. Detergent compositions in particular generally contain a perfume. The perfume is normally simply admixed with the remainder of the detergent composition—whether it is a liquid or solid detergent composition. While the perfume does not add to the performance, it does make the product more aesthetically pleasing and the consumer has come to expect such products to have a pleasing odor.

Perfumes are composed of various volatile substances. Due to these characteristics the perfume is continually emitted from a composition containing same. Various techniques have been developed to hinder or delay the release of the perfume from the composition so that the composition remains aesthetically pleasing for a prolonged length of time. For example, see West German Pat. No. 825,293, Dec. 17, 1951, East German Pat. No. 115,693, Oct. 12, 1975, U.S. Pat. No. 3,772,215, issued Nov. 13, 1973 and U.S. Pat. No. 3,567,119, issued Mar. 2, 1971. While such methods of prolonging the release of perfume from the composition are effective to a limited extent, there is still a need to economically formulate a perfumed particle which continually emits perfume for a substantial length of time.

It will be recognized that desirably a product should initially have a pleasant smell and be capable of delivering that pleasant smell over a long length of time. Encapsulation techniques have a tendency to enclose the perfume such that its perfume emitting properties are not noticeable until actual use of the product, that is when the encapsulating material is dissolved and the perfume is released therefrom. Such techniques generally are expensive also. Sorption techniques of "fixing" perfumes have the drawback of generally low perfume loads and high perfume losses during manufacture. It is desirable in detergent composition usage that the product smell pleasantly while in storage and emit perfume upon addition to water. Prior art methods of encapsulation and sorption have not satisfied these requirements.

It is an object of this invention to formulate a perfumed particle having a high level of perfume and having the capability of emitting perfume over a prolonged time period.

It is another object of this invention to provide a perfumed particle which gives an immediate and long lasting perfume effect and additionally releases perfume upon contact with water.

A still further object of the invention is to provide a perfumed particle made by an efficient and economical process.

It is another object of this invention to formulate a detergent composition containing perfumed particles such that the composition emits perfume for a substantial length of time during storage and upon contact with water.

These and other objects of the invention will become apparent from the description which follows.

As used herein all percents and ratios are by weight unless otherwise indicated.

SUMMARY OF THE INVENTION

Heavily perfumed particles having both immediate and long lasting perfume emitting properties consist essentially of from 30% to 70% water-insoluble perfume, from 25% to 65% of a water-soluble polymer and an effective amount of an emulsifier wherein said particles are comprised of a continuous polymer matrix having dispersed substantially uniformly therethrough perfume/emulsifier droplets of a diameter of from 0.01 microns to 0.5 microns wherein those droplets on the surface of the particle give an immediate perfume effect, those droplets just below the surface give a sustained release of perfume due to migration to the surface and those droplets substantially within the matrix are released upon contact with water.

A process for making the heavily perfumed particles is also provided wherein an aqueous dispersion of perfume, water-soluble polymer and emulsifier is cast upon a drying surface, dried and comminuted to form particles having substantially uniformly dispersed perfume/emulsifier droplets.

Detergent compositions containing the aforementioned perfumed particles are also provided. The detergent compositions consist essentially of a surfactant, optionally detergency adjunct materials and particles of perfume as herein described.

DETAILED DESCRIPTION OF THE INVENTION

The perfumed particles herein are comprised of a continuous water-soluble polymer matrix having dispersed substantially uniformly therethrough perfume/emulsifier droplets. Droplets on the surface of the particle give an immediate perfume effect. Droplets just below the surface give a sustained release perfume due to migration of the perfume to the surface, while those droplets substantially within the matrix are released upon contact with water. The perfumed particles have an ultimate particle size of from 40 microns to 1400 microns, preferably 175 microns to 1000 microns. The perfume/emulsifier droplets contained within the particle have diameters of from 0.01 microns to 0.5 microns, preferably 0.02 microns to 0.2 microns. Further description as to the individual components and process of making are found in the succeeding paragraphs.

Perfume

As used herein the term "perfume" is used to indicate any water-insoluble odoriferous material characterized by a vapor pressure below atmospheric pressure at ambient temperatures. The perfume material will most often be liquid at ambient temperatures. A wide variety of chemicals are known for perfume uses, including materials such as aldehydes, ketones and esters. More commonly, naturally occurring plant and animal oils and exudates comprising complex mixtures of various chemical components are known for use as perfumes. The perfumes herein can be relatively simple in their composition or can comprise highly sophisticated complex mixtures of natural and synthetic chemical components, all chosen to provide any desired odor.

Typical perfumes can comprise, for example, woody/earthy bases containing exotic materials such as sandalwood oil, civet and patchouli oil. The perfumes can be of a light floral fragrance, e.g. rose extract, violet extract, and lilac. The perfumes can also be formulated to provide desirable fruity odors, e.g. lime, lemon and orange. Any material which exudes a pleasant or otherwise desirable odor is used in the perfumed particles herein.

The perfumed particles consist essentially of from 30% to 70% perfume, preferably from 40% to 60% perfume.

Water-soluble Polymer

The matrix of the perfumed particles comprises a water-soluble polymer. As used herein, by "water-soluble polymer" is meant a polymer that will dissolve completely in water at a temperature less than 100° C. Any polymer is used provided it is water-soluble. Examples include water-soluble polyvinyl alcohols, polyethylene glycols, polyvinyl pyrrolidone, poly(ethylene oxide), cellulose derivatives, e.g. cellulose ethers such as methyl-, ethyl-, propyl and butylcellulose ether, butylhydroxybutyl cellulose ether, gelatin and pectin, starches, gum arabic, poly(acrylic acid) and its derivatives, polyacrylamides, styrene maleic anhydrides, poly(vinyl methyl ether maleic anhydrides), amorphous poly(vinyl methyl ether), poly(vinyl 2-methoxyethyl ethers), poly(vinyl sulfonic acid) or its sodium salt, poly(4-vinyl-phthalic acid) and low M.W. melamine formaldehyde resins. Any of the aforementioned polymers which are water-soluble are used herein. Preferred polymers are the polyvinyl alcohols, polyethylene glycols, polyvinyl pyrrolidones, cellulose derivatives, poly(acrylic acid) and its derivatives, the polyacrylamides and poly(ethylene oxides). Most preferred for use herein are the polyvinyl alcohols. Those polyvinyl alcohols which are particularly preferred are the polyvinyl alcohols which have been hydrolyzed to the extent of from 73% to 89%. Such hydrolyzed polyvinyl alcohols are cool water-soluble, economical, and are easy to process.

The perfumed particles consist essentially of from 25% to 65% of the water-soluble polymer, preferably from 35% to 55% of the polymer.

Emulsifier

The emulsifier is used to emulsify the perfume into an aqueous solution of the water-soluble polymer. The perfume, as used at the levels herein, and the water-soluble polymer are not miscible. Processing to form homogeneous particles would not be possible since phase separation of the two components would occur. However, use of an emulsifier causes the perfume to form droplets which are uniformly distributed throughout the polymer solution. The distribution of perfume/emulsifier droplets in the manner achieved herein allows for a heavy loading of perfume in the particles. The emulsifier is used in an amount sufficient to emulsify the perfume in the aqueous solution of the water-soluble polymer. This amount can vary widely depending on the particular perfume, water-soluble polymer or particular emulsifier. Generally, a level of from 0.5% to 6.5% of the emulsifier on a particle basis is sufficient.

Emulsifiers are of a nonionic, anionic or cationic nature. Examples of satisfactory nonionic emulsifiers include fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono- and di-fatty acid esters of ethylene glycol wherein the fatty acid moiety contains from 10 to 20 carbon atoms, fatty acid monoglyceride wherein the fatty acid moiety contains from 10 to 20 carbon atoms, sorbitan esters, polyoxyethylene sorbitol, polyoxyethylene sorbitan, and hydrophilic wax esters. Suitable anionic emulsifiers include the fatty acid soaps, e.g. sodium, potassium and triethanolamine soaps, wherein the fatty acid moiety contains from 10 to 20 carbon atoms. Other suitable anionic emulsifiers include the alkali metal, ammonium or substituted ammonium alkyl sulfates, alkyl arylsulfonates, and alkyl ethoxy ether sulfonates having 10 to 30 carbon atoms in the alkyl moiety. The alkyl ethoxy ether sulfonates contain from 1 to 50 ethylene oxide units. Satisfactory cationic emulsifiers are the quaternary ammonium, morpholinium and pyridinium compounds.

Optional Components

Optional components such as dyes, antioxidants, etc. can be included as a part of the perfumed particles in minor amounts.

Processing

The perfumed particles described above are made by an efficient and economical process. The first step of the process comprises forming an aqueous dispersion consisting essentially of from 2% to 40%, preferably 4% to 25% of the perfume, from 5% to 20%, preferably 10% to 15% of the water-soluble polymer, from 40% to 90%, preferably 60% to 85% water, and sufficient emulsifier, preferably 0.1% to 3% to form a stable emulsion of the perfume in the water-soluble polymer solution. Further processing occurs immediately or after storage.

The aqueous dispersion is cast upon a surface for drying. The nature of the drying surface is not important to the process herein. Thereafter, the cast aqueous dispersion is dried to form a film. Drying can be at ambient temperatures for any required length of time. Optionally, the dispersion is dried at elevated temperatures, e.g. 50° C. to 100° C.

After the dispersion is dried to a film, it is comminuted to form particles of the desired size as above described. Any pulverizing apparatus used for such purposes is suitable herein, e.g. hammer mills, ball mills and impact mills.

Detergent Compositions

The perfumed particles above described are especially useful when included as part of a detergent composition. The detergent composition contains a water-soluble organic surfactant and detergency adjunct materials in addition to the perfumed particles. The level of surfactant depends upon the type of detergency product, but generally ranges from 0.05% to 35%. The organic surfactants are selected from the group consisting of anionic surfactants, nonionic surfactants, ampholytic surfactants, zwitterionic surfactants and mixtures thereof. U.S. Pat. No. 3,664,961, issued May 23, 1972, column 2, line 68 to column 9, line 3 (the disclosure of which is herein incorporated by reference) describes suitable surfactants. The detergent composition is a pre-soak detergent composition, main wash detergent composition, or a household cleaner detergent composition and is in any suitable solid granular or powder form. Pre-soak and household cleaner detergent compositions contain a low level of surfactant, primarily for dispersing the composition throughout the aqueous bath. A level of surfactant from 0.05% to 2%, preferably 0.25% to 1% is used. A main wash detergent composition contains from 5% to 35%, preferably 8% to 20% surfactant.

The balance of the detergent composition consists essentially of a detergency adjunct material. The detergency adjunct material is a builder, soil suspending agent, processing aid, brightener, enzyme, bleach or mixtures thereof. The particular nature of the adjunct materials is dependent on the use of the product. A preferred detergent composition is a built detergent composition containing from 10% to 80%, preferably 25% to 75% detergency builder. Any of the known compounds possessing builder properties are useful herein. U.S. Pat. No. 3,664,961, issued May 23, 1972, column 9, lines 4–35 describes satisfactory detergency builders. (The disclosure of this patent is herein incorporated by reference.)

Detergent compositions herein consist essentially of from 0.1% to 1%, preferably 0.2% to 0.5% of the perfumed particles. The balance of the composition comprises surfactant and detergency adjunct material as above described.

Detergent compositions containing the above-described perfumed particles possess a pleasant smell immediately after making and upon storage for a substantial length of time. Additionally, when the detergent composition is ultimately used in an aqueous solution an additional perfume emittance is noticed. That is, as the particles dissolve in water, additional perfume entrapped within the polymeric matrix is released. Thus, a slight but noticeable perfume effect is obtained during storage while a stronger perfume effect is noticed upon use of the detergent composition.

The following examples are illustrative of the invention.

EXAMPLE I

An aqueous solution is made containing 25.0 gm polyvinyl alcohol (M.W.=90,000 and 98.8% hydrolyzed), 0.5 gm ditallow dimethyl ammonium chloride (as the emulsifier) and 225.0 gm water. The solution is put into a blender and agitated until the polyvinyl alcohol is dissolved. The solution is then allowed to deaerate and cool. Mixing is resumed and 25.0 gm of Cedar Pine perfume is added to the vortex of the agitated solution. The dispersion is agitated vigorously for about 1 minute and then allowed to stand overnight for further deaeration.

The deaerated mix is cast as a 2000 micron film on a flat Lucite sheet and dried overnight. The dried film is then pulverized in a blender with dry ice. (The purpose of the dry ice is to make the film brittle.) The pulverized material is screened to an ultimate size range of from 246 microns to 1,170 microns. The composition of the particles is as follows:

Polyvinyl alcohol: 48.6%
Ditallow dimethyl ammonium chloride: 1.0%
Perfume: 46.5%
Water: 3.9%

Examination by a Scanning Electron Microscope shows the particles have distributed throughout their matrix perfume/emulsifier droplets ranging in diameter from 0.02 microns to 0.2 microns.

The perfumed particles have a slight odor both initially and after prolonged storage. Addition of the particles to water gives an additional perfumed effect, substantially stronger than the initial odor.

Substantially the same results are obtained when other water-soluble polymers, e.g. polyethylene glycol (M.W.=1500), polyvinyl pyrrolidone, methyl cellulose, or polyvinyl methyl ether maleic anhydride are used in place of the polyvinyl alcohol at the same level. However, a stronger odor with these polymers is noted initially and after storage than when polyvinyl alcohol is used as the matrix due to their greater perfume permeability.

Other emulsifiers, e.g. coconut alcohol ethoxylated with 6 moles of ethylene oxide, $C_{12}$ fatty acid monoglyceride, sorbitan monolaurate, $C_{16}$ fatty acid soap, or $C_{12}$ alkyl $(EO)_{12}$ sulfate are used in place of the ditallow dimethyl ammonium chloride at levels ranging from 0.1% to 3% of the aqueous mixture to give substantially the same results.

EXAMPLE II

The process of Example I is followed with proper formulation adjustments to make perfumed particles of the following composition:

Polyvinyl alcohol: 54.5%
Ditallow dimethyl ammonium chloride: 1.1%
Perfume: 41.9%
Water: 2.5%

The particles have an ultimate size range from 300 microns to 1000 microns and are comprised of a PVA matrix with perfume/emulsifier droplets ranging in diameter of from 0.02 to 0.1 microns substantially uniformly distributed throughout.

A perfume odor is easily detected from the particles. A stronger odor is released from the particles on contact with water within 1 to 2 minutes when room temperature water is used and within a few seconds when 72° C. water is used.

EXAMPLE III

An aqueous solution is made up containing 75.0 gm of polyvinyl alcohol (M.W.=10,000 and 88.6% hydrolyzed), 1.5 gm ditallow dimethyl ammonium chloride and 300 gm water. The solution is mixed in a blender, cooled and deaerated.

To 136.6 gm of the solution, with mixing, is added 63.4 gm of Virazon perfume. Upon standing, a perfume layer separates indicating poor emulsification. An additional 0.6 gm of the ditallow dimethyl ammonium chloride is added, bringing the emulsifier level to 4% based on the polyvinyl alcohol. There is no separation of a perfume phase at this level. The dispersion is then cast on a flat Lucite surface at a thickness of 2000 microns. The film is dried and then pulverized in a hammer mill to produce perfumed particles having an ultimate size of from 250 microns to 1,000 microns.

Analysis of the perfumed particles indicate the following composition:

Polyvinyl alcohol: 30.8%
Ditallow dimethyl ammonium chloride: 1.2%
Perfume: 65.9%
Water: 2.1%

Microscopic analysis of the perfumed particles indicate droplets of perfume/emulsifier ranging from 0.02 microns to 0.2 microns. The droplets appear to be uniformly distributed throughout the particle. The particles emit an immediate perfume odor and continue to emit such an odor for a long period of time. Addition of the particles to water releases additional perfume as evidenced by a strong odor.

EXAMPLE IV

A household cleaning composition is formulated as follows:

Sodium sesquicarbonate: 63.8%
Sodium $C_{12}$ alkyl benzene sulfonate: 0.9%
Tall oil ethoxylated with an average of 8 moles ethylene oxide: 0.1%
Trisodium phosphate: 10.0%
Sodium tripolyphosphate: 23.5%
Perfumed particles of Example III: 0.7%
Misc. (coloring matter and water): 1.0%

The composition has a pleasant odor during storage and when made into an aqueous solution prior to use (15 gm product per liter water) emits a strong but pleasing perfume smell.

What is claimed is:

1. Heavily perfumed particles having both immediate and long lasting perfume emitting properties consisting essentially of from 40% to 60% water-insoluble perfume, from 25% to 65% of a water-soluble polymer which will dissolve in water at a temperature of less than 100° C. and which is selected from the group consisting of:
   polyvinyl alcohols,
   polyethylene glycols,
   polyvinyl pyrrolidones,
   cellulose derivatives,
   poly(acrylic acid),
   poly(acrylic acid) derivatives,
   polyacrylamides, and
   poly(ethylene oxides), and from about 0.5% to about 6.5% of an emulsifier selected from the group consisting of nonionic, anionic, and cationic emulsifiers, wherein said particles have an ultimate particle size of from 40 microns to 1400 microns and are comprised of a continuous polymer matrix having dispersed substantially uniformly therethrough perfume/emulsifier droplets of a diameter of from 0.01 microns to 0.5 microns wherein those droplets on the surface of the particle give an immediate perfume effect, those droplets just below the surface give a sustained release of perfume due to perfume migration to the surface and those droplets substantially within the matrix are released upon contact with water.

2. The particles of claim 1 having an ultimate particle size of from 175 microns to 1000 microns.

3. The particles of claim 2 wherein the perfume/emulsifier droplets have a diameter of from 0.02 microns to 0.2 microns.

4. The particles of claim 1 wherein the water-soluble polymer is selected from the group consisting of polyvinyl alcohols, polyethylene glycols, polyvinylpyrrolidone, cellulose derivatives, poly(acrylic acid) and its derivatives, polyacrylamides, poly(ethylene oxides), and mixtures thereof.

5. The particles of claim 4 wherein the water-soluble polymer is polyvinyl alcohol.

6. The particles of claim 5 wherein the polyvinyl alcohol is hydrolyzed to the extent of from 73% to 89%.

7. The particles of claim 5 consisting essentially of from 35% to 55% of the water-soluble polymer and from 40% to 60% of the perfume.

8. A process for producing heavily perfumed particles having both immediate and long lasting perfume emitting properties wherein said particles are comprised of a continuous water-soluble polymeric matrix having dispersed substantially uniformly therethrough perfume/emulsifier droplets, comprising the steps of:
   (a) forming an aqueous dispersion consisting essentially of from 2% to 40% water-insoluble perfume, from 5% to 20% of a water-soluble polymer which will dissolve in water at a temperature of less than 100° C. and which is selected from the group consisting of
   polyvinyl alcohols,
   polyethylene glycols,
   polyvinyl pyrrolidones,
   cellulose derivatives,
   poly(acrylic acid),
   poly(acrylic acid) derivatives,
   polyacrylamides, and
   polyethylene oxides,
   from 40% to 90% water and sufficient emulsifier to emulsify the perfume within the polymer;
   (b) casting the aqueous dispersion of step (a) onto a drying surface;
   (c) drying the dispersion of step (b) to form a film; and
   (d) comminuting the dried film to form the particles having an ultimate particle size of from 40 microns to 1400 microns and distributed therethrough the perfume/emulsifier droplets of a diameter of from 0.01 microns to 0.5 microns, whereby said heavily perfumed particles contain from about 40% to about 60% entrapped perfume and whereby said emulsifier is present in the particles at a level of from about 0.5% to about 6.5% on a particle basis.

9. The process of claim 8 wherein the aqueous dispersion consists essentially of from 4% to 25% of the perfume, from 10% to 15% of the water-soluble polymer, from 60% to 85% of the water and from 0.1% to 3% of the emulsifier.

10. The process of claim 9 wherein the water-soluble polymer is selected from the group consisting of polyvinyl alcohols, polyethylene glycols, polyvinylpyrrolidone, cellulose derivatives, poly(acrylic acid) and its derivatives, polyacrylamides, poly(ethylene oxides) and mixtures thereof.

11. The process of claim 10 wherein the water-soluble polymer is polyvinyl alcohol hydrolyzed to an extent of from 73% to 89%.

12. The process of claim 11 wherein the film is comminuted to produce particles having an ultimate size of from 175 microns to 1000 microns.

13. A detergent composition having both immediate and long term perfume emittance consisting essentially of:
   (a) from 0.05% to 35% of a water-soluble organic surfactant selected from the group consisting of anionic, nonionic, ampholytic, and zwitterionic surfactants and mixtures thereof;
   (b) from 0.1% to 1.0% of the perfumed particles of claim 1; and
   (c) the balance a detergency adjunct material.

14. The detergent composition of claim 13 wherein the water-soluble polymer in the perfumed particles is selected from the group consisting of polyvinyl alcohols, polyethylene glycols, polyvinylpyrrolidone, cellulose derivatives, poly(acrylic acid) and its derivatives, polyacrylamides, poly(ethylene oxides) and mixtures thereof.

15. The detergent composition of claim 14 wherein the water-soluble polymer is polyvinyl alcohol hydrolyzed to the extent of from 73% to 89%.

16. The detergent composition of claim 15 consisting essentially of from 0.05% to 2% of the surfactant.

17. The detergent composition of claim 15 consisting essentially of from 5% to 35% of the surfactant.

18. The detergent composition of claim 17 wherein the detergency adjunct material is a detergency builder.

19. The detergent composition of claim 16 wherein the detergency adjunct material is a detergency builder.

* * * * *